United States Patent [19]

Jackson

[11] Patent Number: 4,649,933
[45] Date of Patent: Mar. 17, 1987

[54] APPARATUS AND METHOD FOR MONITORING BONE-FRACTURE UNION

[75] Inventor: John Jackson, Glasgow, Scotland

[73] Assignee: University of Strathclyde, Glasgow, Scotland

[21] Appl. No.: 649,820

[22] Filed: Sep. 12, 1984

[30] Foreign Application Priority Data

Sep. 17, 1983 [GB] United Kingdom ............... 8324932

[51] Int. Cl.⁴ ............................................... A61B 5/10
[52] U.S. Cl. .................................................... 128/774
[58] Field of Search ............ 128/774, 782, 779, 419 F, 128/419 PT, 82, 83, 92 R, 92 G; 73/763, 855

[56] References Cited

U.S. PATENT DOCUMENTS

| 3,791,375 | 2/1974 | Pfeiffer ........................ | 128/779 |
| 4,152,748 | 5/1979 | Arkans ........................ | 128/779 |
| 4,195,643 | 4/1980 | Pratt, Jr. ...................... | 128/779 |
| 4,444,205 | 4/1984 | Jackson ....................... | 128/782 |

Primary Examiner—William E. Kamm
Attorney, Agent, or Firm—Bell, Seltzer, Park & Gibson

[57] ABSTRACT

A system for monitoring bone union at a bone fracture (13) comprises a fracture cast sleeve (15) to the external surface of which is bonded a transducer (16). Transducer (16) is electrically-conductive and has an electrical resistance which varies with elastic extension and contraction of the transducer. The output of transducer (16) is applied via a resistance-sensitive network (18) to a data evaluating device (20) arranged to normalize signals received from transducer (16) with respect to the time interval during which that signal appears since the signal is of an impulse nature depending upon the rate at which the force is applied to the fracture (13). The normalized signal is further normalized having regard to the mass of the limb concerned and a plurality of such signals are stored in store (30) together with a data log from date data device (32) and these signals are fed to a trend evaluator (34) in order to predict the time interval before bone union occurs.

11 Claims, 7 Drawing Figures

APPARATUS AND METHOD FOR MONITORING BONE-FRACTURE UNION

This invention relates to a system for monitoring union of bone fractures.

Hitherto monitoring of bone fracture union has been undertaken primarily on a manipulative basis by an experienced clinician who by manual means manipulates the two portions of the fractured bone and assesses the degree of movement achievable within the comfort level of the patient. This technique however is non-quantitative and does not lend itself easily to any assessment of when complete union will occur.

In order to obtain an assessment of when complete union will occur it has previously been proposed to affix pins to the two portions of the fractured bone and to mount a strain gage on a side bar interconnecting these pins externally of the limb containing the bone, and thereafter to effect repetitive monitoring of the strain when the limb is subjected to loading. However this proposal has not found favour amongst clinicians because it is invasive, requiring insertion of pins directly into the bone portions, and because the healing rate is affected by the rigidity of the pin and bar structure.

It has previously been proposed to utilise X-ray inspection of the bone fracture site but it has been found that the soft bone-forming tissue or callus is not reflective to X-rays and therefore until after union is complete and the callus has transformed itself into actual bone, no assessment of bone union or of the rate of union has been possible by this technique.

According to the present invention there is provided a bone-fracture union-monitoring system comprising a fracture cast sleeve shaped and dimensioned to fit a patent's limb which contains a bone fracture, the union of which is to be monitored, an elastomeric transducer bonded to the external surface of said sleeve, said transducer being electrically conductive and having an electrical resistance which varies with elastic extension and contraction of the transducer, means for applying a force to said limb to effect a bone movement at the fracture site whereby elastically to extend the transducer in order to vary the electrical resistance thereof, a resistance sensitive electrical network connected to the transducer, and data evaluating means connected to said network and arranged to evaluate the extent of said bone movement at time intervals during progressive union of the bone and consequentially to predict the time lapse until substantially zero bone movement at the fracture site when bone union is completed.

Preferably, the data evaluating means comprises first means for normalising a transducer signal with respect to the time interval during which that signal appears. It will be understood that the transducer tends to provide a signal of an impulse nature depending upon the rate at which the force is applied by the force applying means.

Preferably also, the data evaluating means comprises second means by normalising the signal output by the transducer with respect to the mass of the limb being monitored.

Preferably the data evaluating means comprises a trend analyser adapted to collate previous transducer readings and to evaluate the trend of such readings in order to predict the time interval until substantially zero bone movement at the fracture site or to identify the absence of any such trend which thereby is indicative of an absence of bone union.

It will be understood that a fracture cast sleeve is a known device which is currently fitted to the limb of a patient for the purpose of providing limited elastic support at the fracture site but more particularly for isolating the fracture site from a conventional encasement means such as a plaster of paris cast or a rigid plastics brace. The fracture cast sleeve is a woven elastomeric/fabric which is clinically sterile and is shaped to conform with the limb in question. One example of such a sleeve is marketed by Unied States Manufacturing Company, of U.S.A.

The present invention is applicable to uniform monitoring of fractures in long bones in particular, namely, those of the upper and lower extremities of the human body. The invention is however equally applicable to monitoring of fractures in bones of the extremities in animal bodies.

The elastomeric transducer is preferably a strip of electrically-conductive elastomer sandwiched between strips of non-electrically-conductive elastomer which thereby encase the electrically-conductive elastomer and render it capable of sterilisation. By way of example the conductive elastomer may be U-shaped with electrical leads connected to the free ends of the U-shape. It is preferred that the transducer is made of the materials and manufactured as described in U.S. Patent Specification No. 4,444,205.

An embodiment of the present invention will now be described by way of example with reference to the accompanying drawings, in which.

Figure 3:
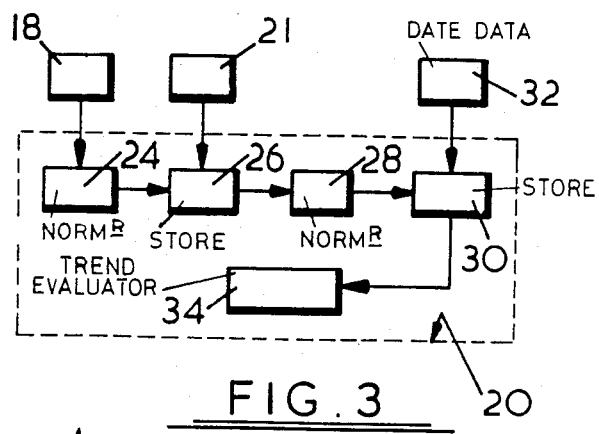
Figure 4:
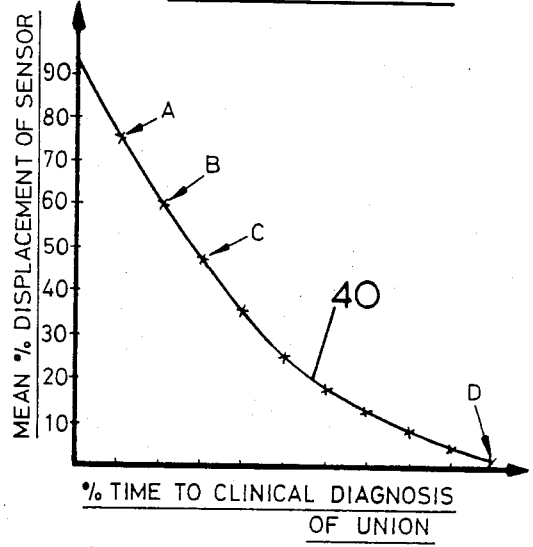

FIG. 3 schematically shows an evaluating device forming part of the present invention;

FIG. 4 illustrates graphically the result of the device of FIG. 3; and

Figure 2:
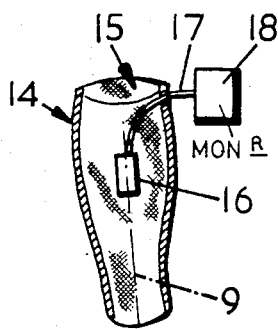
FIG. 2 illustrates the cast arrangement of FIG. 1 in greater detail.
Figure 5:
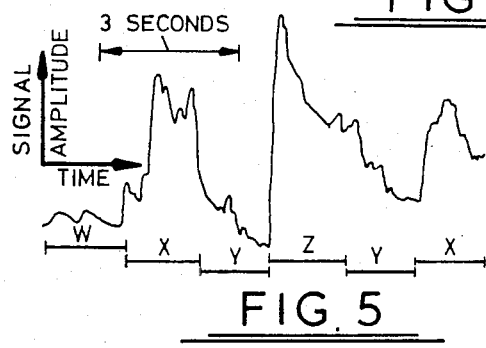
Figure 7:
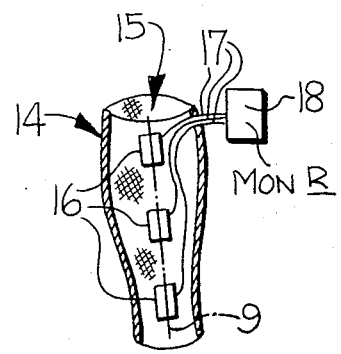
Figure 6:
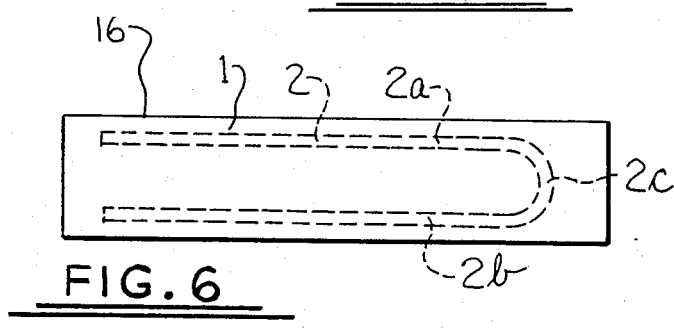

FIG. 5 illustrates graphically a typical waveform of the FIG. 2 arrangement; and FIG. 6 is a schematic diagram illustrating the elastomeric transducer; and FIG. 7 illustrates an alternative cast arrangement similar to FIG. 2.

Figure 1:
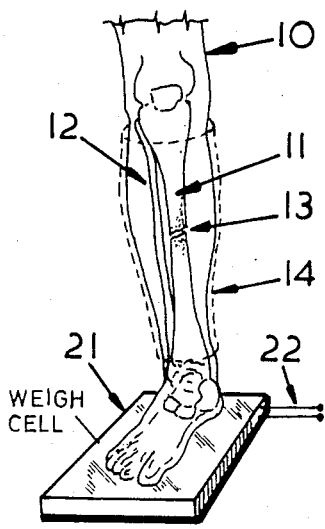
FIG. 1 illustrates a patient's leg having a tibia fracture, the leg being surrounded by a plaster cast arrangement.

As is shown in FIG. 1 a patient's leg 10 having a tibia bone 11 and a fibia bone 12 contains a fracture 13 in the tibia 11 and the leg 10 is encased in a plaster of paris cast 14, the fracture 13 having been appropriately set. FIG. 2 shows the plaster cast 14 partly cut away to reveal a fracture cast sleeve or sock 15 to the front external surface of which is bonded a transducer 16 which is releasably connected by electrical leads 17 to a resistance-sensitive electrical network 18. In the interests of clarity the patient's leg is not shown in FIG. 2, but it will be appreciated that transducer 16 is located on axis 9 on the front surface of sleeve 15 so that it is separated from tibia 11 by a minimal amount of skin and muscle tissue, in preference to being located on a lateral or rear surface of the sleeve 15. Furthermore, in FIG. 2 only one transducer 16 is illustrated and in this case the fracture location longitudinally of the leg 10 requires to be identified in the first instance (for example by X-ray techniques) and a sleeve 15 with an appropriately located transducer 16 selected thereafter for application to the patient's leg 10. In this connection it has been found that only three prepared sleeve types are adequate in practise. Namely with the transducer 16 bonded in an upper region, in a central region (i.e. as shown in FIG. 2) and in a lower region of the sleeve 15.

In order to monitor and assess union of the tibial bone fracture 13 transducer 16 is connected to network 18 and a force is applied longitudinally (in this instance) to the leg 10 by means of transferral of the patient's weight onto leg 10 as quantitatively identified by a weigh cell 21 located beneath the patient's foot. This reading is transferred by leads 22 to an evaluating device 20 shown in FIG. 3, together with the output of network 18. Evaluator 20 comprises a first normalising device 24 which is arranged to receive the pulse-like signal from network 18 and to normalise that signal with respect to the time duration of the pulse. This is effected by pre-programming normaliser 24 with a time interval value representative of the mean pulse duration for a statistically significantly large group of patients undertaking a similar process. The time-normalised peak value of the impulse signal is stored in store 26 as is a signal delivered by weigh cell 21 and representative of the mass of the limb 10 which conveniently is represented by the entire body weight of the patient concerned. A second normaliser 28 is arranged to evaluate from the data stored in store 26 the anticipated time-normalised signal to be expected at a predetermined force level measured in terms of percentage body weight and this data is stored in store 30 together with the date of the reading which is input by means of device 32.

After a suitable time interval within the anticipated time scale of the fracture union, which in the case of a tibial fracture is of the order of 10 weeks after the fracture has been set and the plaster of paris cast 14 applied, further sets of readings are taken and stored in stores 26 and 30. When store 30 has accumulated 3 or more readings these are fed to trend analyser 34 which analyses the readings on a time scale determined by the date data contained in store 30 and if any trend is apparent (as determined by a conventional curve fitting programme) identifies that trend and outputs a reading being a prediction of the time lapse until substantially zero bone movement at the fracture 13.

A typical set of data showing progressive union is illustrated in the graph of FIG. 4 from which it will be seen that initially when the fracture is set and cast 14 applied the transducer output signal is of the order of 90 units but as time elapses the transducer output signal drops progressively until readings of less than 10 units are achieved as union becomes practically complete. At complete union, as diagnosed clinically by a conventional technique, the transducer output signal is of the order of one or two units only. It will be observed that the curve 40 is continuous nad it has been found over a statistically significantly large group of patients to be of consistent shape and it is on this basis that the trend analyser 34 operates to predict the time interval to union from only a small number of individual sampling points on the curve for any particular patient within a short time interval after bone setting. That is to say, the data collected may be represented in FIG. 4 by the points A,B and C and trend analyser 34, in accordance with its curve fitting programme, predicts point D and more particularly the time interval between points C and D.

It will be observed that the system according to the present invention is non-invasive and is dependent only upon a level of force applied to the limb in accordance with the comfort level of the patient in that it is the patient himself who applies the force to the limb by weight transferral. By way of example this weight transferral may be of the order of 20–40% of the patient's body weight in the case of the tibial fracture 13. FIG. 5 illustrates the output waveform of a transducer 16 as a result of a patient with an unfused fracture of the left tibia moving into four different positions. Portion W of the waveform results with the patient sitting in a chair; portion X which occurs twice results from the patient standing on both legs but it will be noticed that the signal amplitude is greater in the first occurrance of X than in the second occurrance indicating a greater weight transferral to the left leg on the first occurrance of X; portion Y which occurs with the patient standing only on his right leg (i.e. the non-fractured leg); and portion Z which results with the patient standing solely on his left leg (i.e. the fractured leg). It will be seen that the differing peak amplitudes of portions X,Z and X is consequential on the differing percentages of body weight applied to the left leg by this patient and it is for this reason that normaliser 28 is required, whilst the time durations of portions X, Z and X are substantially the same because there is only one patient involved. A different patient would display different time durations on the X, Z and X portions of the comparable waveform and it is for this reason that normaliser 24 is required.

It is also to be understood that the effect of applying a compressive force to tibia 11 as is illustrated in the embodiment, is to cause a lateral movement at the site of fracture 13 which lateral movement effects extension of transducer 16 by elongation of the transducer between its upper and lower ends both of which remain substantially immobile. In other words the transducer extension is caused by a bulging of a central portion of the transducer. The transducer 16 is preferably composed of a U-shaped strip 2 (FIG. 6) of electrically-conductive elastomer sandwiched between strips 1 of non-electrically-conductive elastomer effecting an encasement of the conductive strip. The U-shape may lie in the general plane of the front surface of sleeve 15 but preferably lies perpendicularly to that plane so that transducer bulging caused by bone movements at fracture 13 strains both limbs of the U-shape, thereby enhancing signal strength from the transducer 16.

In accordance with the present invention the transducer may also take the form of a three separate transducers 16 simultaneously bonded to sleeve 15 along line 9 (FIG. 7), one such transducer being located in the upper leg portion, one in the central leg portion, and one in the lower leg portion. With this arrangement only the one transducer 16 overlying the site of the fracture is connected to the normaliser 24 via the network 18 for the purpose of providing bone movement data whilst either or both of the other two transducers are connected into network 18 to provide muscle-noise signals for reduction of the bone-movement data signal on a common-mode rejection basis. This arrangement in addition to providing for data signal enhancement simplifies storage by reducing the inventory of sleeves 15.

Each transducer 16 referred to previously is preferably provided with low-extension/high signal output characteristics and low tear strength having regard to the required duty cycle of elastic extensions which are only of the order of 2% or less.

In accordance with the present invention the force applying means may be compressive as previously described or tensile or torsional. For example, in the case of a fractured tibia, the force may simply be applied at the site of fracture 13 by raising the leg from the vertical position to a horizontal position. Alternatively the weigh cell may be arranged vertically in order to measure a horizontal force generated by the patient.

It will be understood that although the invention has been described in particular terms with reference to a fractured tibia its application is not limited either to tibial fractures or even to leg fractures and whilst it is desirable to have the limb containing the fracture encased either by a plaster of paris cast or by a brace this is not necessary for the purposes of applying the monitoring system of the present invention. Such encasement means however does limit the maximum bone movement at the site of the fracture and is therefore a safety feature. Furthermore because the present invention does not utilise reported doses of X-rays, there is no need for the patient to enter a hazardous environment. Furthermore because in the preferred arrangement the sensor is made of elastomeric materials it is unaffected by the environmental conditions which pertain inside the encasement means. The transducer which is primarily made of elastomeric material is of course bonded to the fracture cast sleeve by an elastomeric bonding agent such as a silicone rubbber extending throughout the areal extent of the transducer.

What is claimed is:

1. A non-invasive bone-fracture union-monitoring system comprising a preformed fracture cast sleeve for fitting to a patient's limb containing a bone fracture the union of which is to be monitored, an elastomeric transducer adherent to the external surface of said sleeve at a predetermined location thereon, said transducer being electrically conductive and having an electrical resistance which varies with elastic extension and contraction of the transducer, means for establishing a measure of the mass of the limb containing the bone-fracture, a resistance sensitive electrical network connected to the transducer to measure variations in the electrical resistance of the transducer when a force is applied to the limb to effect lateral bone movement at the fracture site, and data evaluating means connected to said network and arranged to evaluate the extent of said bone movement at measured time intervals during progressive union of the bone and consequentially to predict the time lapse until substantially zero bone movement at the fracture site when bone union is completed.

2. A system as claimed in claim 1, wherein the data evaluating means comprises means connected to the output of said network for normalising a transducer signal with respect to the time interval during which that signal appears.

3. A system as claimed in claim 2, wherein the data evaluating means comprises means connected to the output of the time normalising means for normalizing the signal output by the transducer with respect to the mass of the limb being monitored.

4. A system as claimed in claim 3, wherein the data evaluating means comprises means to collate a plurality of previous normalised transducer readings and to evaluate the trend of such readings by curve-fitting to a predetermined curve in order to predict the time interval until substantially zero bone movement at the fracture site.

5. A system as claimed in claim 3, wherein the data evaluating means comprises means to collate previous normalised transducer readings and to identify the absence of any trend therein to thereby indicate absence of progressive bone union.

6. A system as claimed in claim 1, wherein the elastomeric transducer comprises a strip of electrically-conductive elastomer sandwiched between strips of non-electrically-conductive elastomer which thereby encase the electrically-conductive elastomer.

7. A system as claimed in claim 6, wherein the conductive elastomer is U-shaped with electrical leads connected to the free ends of the U-shape.

8. Apparatus for use in a bone fracture union monitoring system in which lateral movement of the bone fracture is measured, said apparatus comprising a fracture cast sleeve of an elastomeric fabric for conforming to the shape of a human limb and to surround and support a patient's limb at the fracture site and an elastomeric transducer adherently secured to the external surface of said sleeve at a predetermined location thereon, said transducer comprising an electrically conductive elastomeric material having an electrical resistance which varies with elastic extension and contraction of the transducer, whereby extension and contraction of the transducer due to lateral bone movement at the fracture site may be detected.

9. Apparatus as claimed in claim 8 wherein said apparatus includes a plurality of like transducers individually adherent to the external surface of said sleeve at different predetermined locations longitudinally of said sleeve.

10. Apparatus as claimed in claim 8 wherein said plurality of like transducers extend along a line at the front surface of the sleeve.

11. A method of non-invasively monitoring bone union at a bone-fracture in a patient's limb, said method comprising providing a preformed fracture cast sleeve having an elastomeric transducer adherent at a predetermined location on the external surface of said sleeve the transducer being electrically conductive and having an electrical resistance which varies with elastic extension and contraction thereof, fitting said sleeve to said limb with said transducer adjacent the bone-fracture site, intermittently within the anticipated time scale of the fracture union connecting the transducer to a resistance sensitive network, imposing a force on the bone fracture site during each such connection and measuring the amplitude and duration of the electrical resistance-change signal output by the transducer as monitored by the resistance-sensitive network and indicative of limited lateral bone movement at said site, storing a plurality of such measurement readings together with the dates on which said readings were recorded and a measure of the mass of the limb containing the fracture site, and analyzing the stored readings on a time scale determined by the date data by curve-fitting with a curve predetermined by said mass measure to identify a trend in the readings and thereby predict the time lapse until substantially zero bone movement at the bond-fracture site when bone union is completed.

* * * * *